US010525144B2

(12) United States Patent
Cui et al.

(10) Patent No.: US 10,525,144 B2
(45) Date of Patent: Jan. 7, 2020

(54) SELECTIVE TARGETING OF AN ANTI-INFLAMMATORY RECEPTOR IN HUMAN MITOCHONDRIA AND PRESERVATION OF MITOCHONDRIAL FUNCTIONS

(71) Applicant: THE JOHNS HOPKINS UNIVERSITY, Baltimore, MD (US)

(72) Inventors: Honggang Cui, Lutherville-Timonium, MD (US); Peter M. Abadir, Woodstock, MD (US); Jeremy D. Walston, Baltimore, MD (US); Andrew G. Cheetham, Charlottesville, VA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/525,435

(22) PCT Filed: Nov. 10, 2015

(86) PCT No.: PCT/US2015/059899
§ 371 (c)(1),
(2) Date: May 9, 2017

(87) PCT Pub. No.: WO2016/077311
PCT Pub. Date: May 19, 2016

(65) Prior Publication Data
US 2018/0289824 A1 Oct. 11, 2018

Related U.S. Application Data

(60) Provisional application No. 62/077,706, filed on Nov. 10, 2014.

(51) Int. Cl.
*A61K 47/64* (2017.01)
*A61K 47/65* (2017.01)
(Continued)

(52) U.S. Cl.
CPC ............. *A61K 47/64* (2017.08); *A61K 31/41* (2013.01); *A61K 31/4178* (2013.01);
(Continued)

(58) Field of Classification Search
CPC ........ A61K 38/10; A61K 38/16; A61K 38/17; A61K 38/1709; A61K 47/64;
(Continued)

(56) References Cited

U.S. PATENT DOCUMENTS

2008/0146642 A1* 6/2008 Kong .................. C07C 309/15
514/406
2011/0245146 A1 10/2011 Payne
(Continued)

OTHER PUBLICATIONS

International Search Report and Written Opinion for International Application No. PCT/US15/59899 dated Mar. 8, 2016.

*Primary Examiner* — Jeffrey E. Russel
(74) *Attorney, Agent, or Firm* — Tarolli, Sundheim, Covell & Tummino LLP (57) ABSTRACT

The present invention provides compounds and a method for the targeted delivery of Mitochondrial Angiotensin Receptor Blockers (MARBs) to the Mitochondrial Angiotensin System (MAS) for the treatment of diseases caused by angiotensin-related mitochondrial dysfunction. The compounds include a mitochondrial targeting signal, a residue of a drug molecule, a functional moiety, and a scaffold moiety.

40 Claims, 5 Drawing Sheets

Specification includes a Sequence Listing.

(51) Int. Cl.
      *A61K 49/18* (2006.01)
      *A61K 49/00* (2006.01)
      *A61K 31/41* (2006.01)
      *A61K 31/4178* (2006.01)
      *A61K 31/4184* (2006.01)
      *A61K 31/4245* (2006.01)

(52) U.S. Cl.
      CPC ...... *A61K 31/4184* (2013.01); *A61K 31/4245* (2013.01); *A61K 47/65* (2017.08); *A61K 49/0017* (2013.01); *A61K 49/0041* (2013.01); *A61K 49/0054* (2013.01); *A61K 49/0056* (2013.01)

(58) Field of Classification Search
      CPC .. A61K 47/641; A61K 47/65; A61K 49/0017; A61K 49/0043; A61K 49/0054; A61K 49/0056; C07K 7/08; C07K 14/00; C07K 14/47
      See application file for complete search history.

(56) References Cited

U.S. PATENT DOCUMENTS

| | | | |
|---|---|---|---|
| 2014/0135275 A1 | 5/2014 | Keefe et al. | |
| 2014/0303081 A1 | 10/2014 | Dhar et al. | |
| 2015/0258204 A1* | 9/2015 | Yang | A61K 47/48215 525/410 |
| 2017/0014361 A1* | 1/2017 | Dhar | A61K 41/0042 |
| 2017/0216219 A1* | 8/2017 | Dhar | A61K 31/573 |

* cited by examiner

```
                         SEQUENCE LISTING

<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: Synthetic Construct

<400> SEQUENCE: 1

Met Leu Arg Ala Ala Leu Ser Thr Ala Arg Arg Gly Pro Arg Leu Ser
1               5                   10                  15

Arg Leu Leu

<210> SEQ ID NO 2
<211> LENGTH: 19
<212> TYPE: PRT
<213> ORGANISM: Artificial Sequence
<220> FEATURE:
<223> OTHER INFORMATION: Synthetic Construct

<400> SEQUENCE: 2

Met Leu Ser Ala Arg Ser Ala Ile Lys Arg Pro Ile Val Arg Gly Leu
1               5                   10                  15

Ala Thr Val

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Met Ser Val Leu Thr Pro Leu Leu Leu Arg Gly Leu Thr Gly Ser Ala
1               5                   10                  15

Arg Arg Leu Pro Val Pro Arg Ala Lys
            20                  25

<210> SEQ ID NO 4
<211> LENGTH: 8
<212> TYPE: PRT
<213> ORGANISM: Artificial Sequence
<220> FEATURE:
<223> OTHER INFORMATION: Syntehtic Construct

<400> SEQUENCE: 4

Asp Arg Val Tyr Ile His Pro Phe
1               5

<210> SEQ ID NO 5
<211> LENGTH: 21
<212> TYPE: PRT
<213> ORGANISM: Artificial Sequence
<220> FEATURE:
```

-continued

```
<223> OTHER INFORMATION: Synthetic Construct

<400> SEQUENCE: 5

Met Leu Arg Ala Ala Leu Ser Thr Ala Arg Arg Gly Pro Arg Leu Ser
1               5                   10                  15

Arg Leu Leu Cys Lys
            20
```

SELECTIVE TARGETING OF AN ANTI-INFLAMMATORY RECEPTOR IN HUMAN MITOCHONDRIA AND PRESERVATION OF MITOCHONDRIAL FUNCTIONS

RELATED APPLICATIONS

This application is the U.S. national phase of International Patent Application No. PCT/US2015/059899, filed Nov. 10, 2015, which claims the benefit of priority of U.S. Provisional Application 62/077,706, filed Nov. 10, 2014, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Nov. 30, 2018, is named JHU-026950 US PCT Sequence Listing_ST25.txt and is 1690 bytes in size.

BACKGROUND

The Renin Angiotensin System (RAS) is a key regulator of cardiovascular and renal function. Although many studies have focused on the impact of extracellular angiotensin II and its receptors Angiotensin II type 1 ($AT_1R$) and Angiotensin II type 2 ($AT_2R$) on the cardiovascular system, others have reported that angiotensin II is also present in the intracellular compartment and can be released upon cell stretch to mediate cellular growth and/or apoptosis[1-3]. While many of the autocrine effects of this endogenous angiotensin store are believed to be mediated by plasma membrane angiotensin receptors, an intracellular RAS acting on nuclear angiotensin receptors has also been proposee[4,5].

The RAS influences cardiovascular function via nitric oxide regulation[6-8]. $AT_1R$ blockade increases nitric oxide (NO) and this increase is abolished by concomitant $AT_2R$ blockade, suggesting that the $AT_2R$ is important in NO production[9]. $AT_2R$ likely increases NO production via direct stimulation of Nitric Oxide Synthase (NOS)[10] or indirectly through bradykinin-dependent mechanisms[6,7]. Very recently, the intracrine activation of $AT_2R$ has been reported to increase the production of NO in isolated cortical kidney nuclei[11].

Possible sources of NO coupled to angiotensin signalling include the three canonical NOS isoforms; neuronal (nNOS), inducible (iNOS), and endothelial NOS (eNOS)[1]. Additionally, there have been reports of a NOS isoform in mitochondria (mtNOS)[13,14]. Though the unique identity of mtNOS is still controversial[15], this mitochondria-specific isoform has been localized to the inner mitochondrial membrane, where it may regulate mitochondrial respiration[13,16,17]. While several studies have provided evidence that angiotensin receptors can couple to the canonical NOS isoforms[7,18], nothing is known about whether intracellular angiotensin II influences mitochondrial NO production or if it has any other effects on mitochondrial function.

Subcellular localization of a functional Mitochondrial Angiotensin System (MAS) coupled to angiotensin receptors was recently documented (U.S. Provisional Patent Application No. 61/231,529, the contents of which is incorporated herein by reference), which opens a new area of investigation into the regulation of mitochondrial function by angiotensin II-mediated intracrine signalling. The presence and function of a MAS was investigated via high resolution transmission immunoelectron microscopy, confocal imaging in live cells tracking the expression of angiotensin receptors and real time measurement of mitochondrial NO production and respiration in response to activation or inhibition of the receptor(s) in isolated mitochondria. Functional angiotensin II type 2 receptors are present on the mitochondrial inner membrane and are colocalized with endogenous angiotensin II. Activation of the mitochondrial angiotensin system (MAS) is coupled to mitochondrial nitric oxide production and can modulate respiration. The localization of $AT_2R$ in the mitochondrial inner membrane suggests its importance to nitric oxide production, which is believed to originate in the inner membrane through mtNOS[19-21]. Based on these recent findings of a functional mitochondrial angiotensin system and the beneficial effects of $AT_1R$ blockers on mitochondrial number and function, such a beneficial effect might be mediated via unopposed $mtAT_2R$.

Mitochondria play a key role in the regulation of energy metabolism, reactive oxygen species (ROS) production and apoptosis, and so mitochondria provide an attractive drug target. Although systemic administration of angiotensin receptor blockers (ARBs) has been documented to improve mitochondrial functions, such administration is limited, often in older populations, by its impairment of renal function and its effects on blood pressure. Moreover, the need to use a high concentration of a drug to achieve an effective local concentration at the disease site often results in accompanying nonspecific toxic side effects.

Therefore, there remains a need to develop methods for selectively targeting the mitochondrial angiotensin receptor, $mtAT_2R$, for therapeutic intervention for the treatment of cardiovascular, renal, neurological, and musculoskeletal disorders associated with aging and mitochondrial dysfunction.

SUMMARY OF THE INVENTION

The present invention provides compounds comprising a mitochondrial targeting signal, a residue of a drug molecule, a functional moiety, and a scaffold moiety; wherein the mitochondrial targeting signal is a peptidic moiety; and the mitochondrial targeting signal, the residue of a drug molecule, and the functional moiety are each covalently linked to the scaffold moiety. The functional moiety comprises a cell-targeting peptidic moiety, a cell-penetrating peptidic moiety, a fusogenic peptidic moiety, a histidine-rich moiety, a fluorophore, or a residue of a second drug molecule; wherein the fluorophore is selected from optionally substituted boron-dipyrromethene (BODIPY), coumarin, anthracene, tetrapyrrole, and cyanine derivatives.

In certain embodiments, the present invention provides a pharmaceutical preparation suitable for use in a human patient for the treatment of an angiotensin-related mitochondrial dysfunction-caused disease.

In certain embodiments, the present invention provides methods for treating a disorder associated with mitochondrial dysfunction by administering a compound of the invention.

BRIEF DESCRIPTION OF THE DRAWINGS

FIG. 8 consists of panels A-J. Panels A and B are images showing quantification of mitochondrial membrane potential based on TMRE localization in control (panel A) and $MTS_1$-Ls-5-FAM-treated (panel B) cardiac cells. TMRE localizes in the mitochondria, and based on the intensity of the TMRE dye, the mitochondrial membrane potential can be calculated (panel C). The maximum TMRE intensity per pixel shows no significant difference between control and $MTS_1$-Ls-5-FAM (panels E and F), suggesting that treatment with $MTS_1$-Ls-5-FAM did not affect the overall health of the mitochondria. However the coefficient of variation (panel G) shows a significant difference, meaning that $MTS_1$-Ls-5-FAM treatment caused more mitochondria to be either extremely activated or extremely de-activated (as determined per total mitochondria (panel I) or per total cells (panel J)).

DETAILED DESCRIPTION OF THE INVENTION

The present invention is based on the surprising discovery of a class of compounds that can selectively deliver therapeutic agents to the mitochondria. The compositions provided herein relate to a therapeutic conjugates comprising a drug-derived moiety and a mitochondrial targeting signal. The compounds and methods described herein can enable selective delivery of a Mitochondrial Angiotensin Receptor Blocker (MARB) to the Mitochondrial Angiotensin System (MAS) for the treatment of angiotensin-related mitochondrial dysfunction-caused disease. By targeting mitochondrial $AT_1R$, rather than better-known vascular receptors, the methods and compounds of the invention provide an important new mechanism for drug delivery, which can be applied to conditions related to aging, such as sarcopenia.

Accordingly, in certain embodiments, the present invention provides a compound comprising a mitochondrial targeting signal, a residue of a drug molecule, a functional moiety, and a scaffold moiety, wherein the mitochondrial targeting signal, the residue of a drug molecule, and the functional moiety are each covalently linked to the scaffold moiety.

Further modification of the compounds of the invention enables a user to study the cellular localization of the conjugate, when can be utilized to fine-tune a therapeutic regimen. Accordingly, the compound further comprises a functional moiety covalently linked to the scaffold moiety, the functional moiety comprising a cell-targeting peptidic moiety, a cell-penetrating peptidic moiety, a fusogenic peptidic moiety, a histidine-rich moiety, a fluorophore, or a residue of a second drug molecule. Each of these functional moieties are described herein.

"Peptidic", as used herein, refers to any amino acid based moiety that can comprise natural, modified and/or unusual amino acids, pseudopeptides or peptidomimetics. The following conventional three(one)-letter amino acid abbreviations are used herein: Ala(A)=alanine; Aca=aminocaproic acid, Arg(R)=arginine; Asn(N)=asparagine; Asp(D)=aspartic acid; Cit=citrulline; Cys(C)=cysteine; Gln(Q)=glutamine; Glu(E)=glutamic acid; Gly(G)=glycine; His(H)=histidine; Ile(I)=isoleucine; Leu(L)=leucine; Lys(K)=lysine; Met(M)=methionine; Orn=ornithine; Phe(F)=phenylalanine; Pro(P)=proline; Ser(S)=serine; Thr(T)=threonine; Trp(W)=tryptophan; Tyr(Y)=tyrosine; and Val(V)=valine. Use of the prefix D- indicates the D-isomer of that amino acid; for example D-lysine is represented as D-Lys.

Modified amino acids which can be used to practice the invention include, but are not limited to, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "pseudopeptide" or "peptidomimetic" is a compound which mimics the structure of an amino acid residue or a peptide, for example, by using linking groups other than via amide linkages (pseudopeptide bonds) and/or by using non-amino acid substituents and/or a modified amino acid residue. A "pseudopeptide residue" means that portion of a pseudopeptide or peptidomimetic that is present in a peptide. The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

Mitochondrial Targeting Signals

Mitochondria are unique sub-cellular organelles that possess their own DNA and RNA and mechanisms for their translation, yet they express only 10% of the proteins that they contain. Instead, mitochondria rely in part on the translation products of nuclear genes. These products traverse the cytoplasm and are 'imported' into the mitochondria via a system of outer- and inner-membrane-bound protein complexes, where they are delivered to the appropriate mitochondrial compartment and rendered active.

This mitochondrial import process is regulated by an N-terminal presequence in the nuclear gene of the protein that tags the protein with a sequence that tells the import machinery where the protein should be delivered—these are known as Mitochondrial Targeting Signal (MTS) peptides[22]. Once the protein has been transported to the desired compartment, the MTS portion of the protein may be removed by a mitochondrial peptidase, allowing the protein to fold into its functional state and become active.

Because MTS peptides are recognized with specificity, the MTS peptides enable transport of non-mitochondrial proteins into the mitochondria, and have been examined in the transport of other macromolecules[23].

In certain embodiments, the mitochondrial targeting signal used in the compounds of the invention is a peptidic moiety. In certain embodiments, the mitochondrial targeting signal directs delivery of the compound to a mitochondrion. In certain embodiments, mitochondrial targeting signal directs delivery of the compound selectively to a compartment of a mitochondrion. For example, the mitochondria targeting signal can selectively direct a compound to an outer membrane, an inner membrane, and inter-membrane space, or a mitochondrial matrix.

In certain embodiments, the mitochondrial targeting signal is recognized and cleaved from the compound in the mitochondria by a mitochondrial peptidase. In certain embodiments, this recognition and cleavage occurs in a particular compartment of the mitochondria. Mitochondrial Processing Peptidases (MPP) are responsible for cleaving the majority of mitochondrial proteins. Two others cleave certain subsets: Inner-membrane peptidase (IMP) and mitochondrial intermediate peptidase (MIP). In certain embodiments, MPP that cleaves the MTS sequence, enabling release of the drug residue.

In certain embodiments, only a portion of the conjugates of the invention that are taken up by the mitochondria becomes functionally activated after cleavage by mitochondrial peptidase. Once in mitochondria, the drug molecule can bind to the target mitochondrial angiotensin II receptor and elicit changes in mitochondrial bioenergetics and free radical generation.

In certain embodiments, the mitochondrial targeting signal comprises 10-80 amino acid residues. In certain embodiments, the mitochondrial targeting signal comprises 10-70 amino acid residues. More preferably, the mitochondrial targeting signal comprises 10 to 50, 10 to 40, 10 to 30, 10 to 25, or 10 to 20 amino acid residues. In certain preferred embodiments, the mitochondrial targeting signal comprises 10 to 30 amino acid residues.

In certain embodiments, the mitochondrial targeting signal comprising an amphipathic helix structural motif. In order to adopt the amphipathic helix structural motif, the mitochondrial targeting signal can be enriched in basic (e.g., Arg, Lys), hydroxylated (e.g., Ser, Thr) and/or hydrophobic (e.g., Ala, Leu, Ile) residues. In certain embodiments, the mitochondrial targeting signal comprising an amphipathic helix structural motif exhibit alternating hydrophobic and hydrophilic segments.

In certain embodiments, pre-sequences of mitochondrial matrix proteins include, but are not limited to, F1-ATPase β, COX IV, Rhodanese, and Thiolase[24-26].

In certain embodiments, the mitochondrial targeting signal comprises an amino acid sequence having at least 50%, 60%, 70%, 80%, 90%, or 95% sequence homology to Met-Leu-Arg-Ala-Ala-Leu-Ser-Thr-Ala-Arg-Arg-Gly-Pro-Arg-Leu-Ser-Arg-Leu-Leu (SEQ ID NO: 1), Met-Leu-Ser-Ala-Arg-Ser-Ala-Ile-Lys-Arg-Pro-Ile-Val-Arg-Gly-Leu-Ala-Thr-Val (SEQ ID NO: 2),[27] or Met-Ser-Val-Leu-Thr-Pro-Leu-LeuLeu-Arg-Gly-Leu-Thr-Gly-Ser-Ala-Arg-Arg-Leu-Pro-Val-Pro-Arg-Ala-Lys (SEQ ID NO: 3).[28] In certain embodiments, the mitochondrial targeting signal comprises an amino acid sequence of SEQ ID NO: 1.

In certain embodiments, the mitochondrial targeting signal is covalently linked to the scaffold moiety through one or more covalent bonds. Exemplary covalent bonds through which the mitochondrial targeting signal can be attached to the scaffold moiety include amide, carbonate, carbamate, ether, ester, sulfonate, and sulfamate. The mitochondrial targeting signal can be covalently attached to the scaffold at any reactive position of the mitochondrial targeting signal. In certain embodiments, such reactive positions include reactive heteroatoms on a side chain of an amino acid residue, a reactive N-terminus of a peptidic moiety, or a reactive C-terminus of a peptidic moiety. Exemplary amino acid residues having reactive side chain moieties include Arg, Lys, Asp, Glu, Ser, Thr, Asn, Gln, Cys, Sec, and Pro. In preferred embodiments, the reactive position of the mitochondrial targeting signal that is covalently linked to the scaffold is a functionalizable C-terminus of a peptidic moiety. In certain embodiments, the mitochondrial targeting signal covalently linked to the scaffold forms a continuous peptide chain.

Scaffolds

The compounds of the invention comprise a mitochondrial targeting signal, a residue of a drug molecule, and a functional moiety, linked through the intermediacy of a scaffold moiety.

In certain embodiments, the scaffold moiety comprises one or more covalent bonds, which can include amide, carbonate, carbamate, ether, ester, sulfonate, and sulfamate. In certain embodiments, the scaffold comprises a peptide fragment, an oligocarboxylate, or an oligomeric moiety.

In certain embodiments, the scaffold comprises one or more functionalizable heteroatoms. These functionalizable heteroatoms can form covalent attachments with, for example, the mitochondrial targeting signal, a fluorophore, a cell-targeting peptidic moiety, a cell-penetrating peptidic moiety, or another functional group.

In preferred embodiments, the scaffold comprises a peptide fragment comprising from 1 to 20, 1 to 10, 1 to 8, 1 to 6, 1 to 5, 1 to 4, 1 to 3, 1 or 2 amino acid residues. In certain embodiments, the peptide fragment comprises at least one amino acid residue comprising a functionalizable side chain moiety. In certain embodiments, the peptide fragment comprises at least one amino acid residue selected from Arg, Lys, Asp, Glu, Ser, Thr, Asn, Gln, Cys, Sec, and Pro. In certain embodiments, the peptide fragment comprises at least one amino acid residue selected from Lys, Asp, Glu, and Cys, preferably selected to provide two or more functional groups with differential reactivity to permit selective sequential functionalization of the two or more functional groups. For example, if one functional group is a carboxylic acid and another is a thiol, the thiol will preferentially react under nucleophilic substitution conditions, and then the carboxylic acid can be coupled with an amine or alcohol to form an amide or ester, respectively. In particular embodiments, the scaffold moiety comprises Cys-Lys. In certain embodiments in which the scaffold moiety is a peptide fragment, the C-terminus of the peptide fragment is amidated.

In embodiments in which the scaffold moiety is a peptide fragment, the mitochondrial targeting signal can form a continuous peptide chain with the scaffold moiety. In certain such embodiments, the N-terminus of the peptide fragment of the scaffold moiety is attached to the mitochondrial targeting signal.

Therapeutic Agents

In certain embodiments, the drug molecules used in the compounds of the invention bind to an angiotensin receptor. In certain embodiments, the drug molecules bind to an angiotensin II receptor. Angiotensin II receptors include $AT_1$-type receptors and $AT_2$-type receptor.

In certain embodiments, the drug molecule exerts an antagonistic effect on an angiotensin II receptor. For example, the drug molecule can be an angiotensin receptor blocker or a mitochondrial angiotensin receptor blocker. Mitochondrial angiotensin receptor blockers can modulate the mitochondrial-angiotensin system (MAS), and thereby are useful in treating angiotensin-related mitochondrial dysfunction.

The inventors recently discovered functional mitochondrial Angiotensin receptors ($mtAT_1R$ and $mtAT_2R$) that shift to an increased $mtAT_1R/mtAT_2R$ ratio with aging. One of the protective benefits of Angiotensin (Ang) receptor type 1 ($AT_1R$) blockers, such as Losartan (LOS), arises from its systemic effects on blood pressure and remodelling. The inventors further discovered that mitochondrial function can be improved by LOS, and high doses of LOS accelerate skeletal muscle healing and prevent disuse atrophy in older mice. Therefore, angiotensin receptor blockers such as Losartan have utility beyond hypertension treatment; angiotensin receptor blockers can be used in the treatment of conditions relevant to older adults.

In certain embodiments, the angiotensin receptor blocker is valsartan, telmisartan, losartan, irbesartan, azilsartan, olmesartan, candesartan, or ephrosartan. In particular embodiments, the drug molecule is losartan.

In certain embodiments, the drug molecule is covalently linked to the scaffold moiety through one or more covalent bonds. Exemplary covalent bonds through which the drug molecule can be attached to the scaffold moiety include amide, carbonate, carbamate, ether, ester, sulfonate, and sulfamate. The drug molecule can be covalently attached to the scaffold any substitutable position of the drug molecule.

Figure 2:
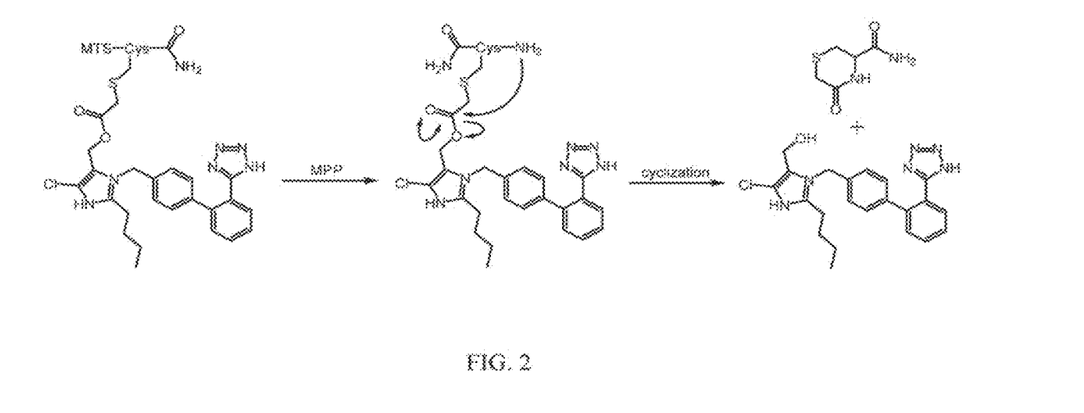
FIG. 2 is a scheme showing the proposed mechanism for the release of free Losartan via mitochondrial processing peptidase proteolysis and subsequent cyclization of the cleavage product.

In certain embodiments, the residue of the drug molecule is effectively a prodrug. One or more covalent bonds linking the residue of the drug molecule to the scaffold moiety can be cleavable in the mitochondria, thereby releasing the drug molecule (e.g., a mitochondrial angiotensin receptor blocker) in the mitochondria or a desired compartment of the mitochondria. FIG. 2 depicts an exemplary mechanism for release of the drug molecule. Exemplary groups that are cleavable under physiological conditions include hydrolyzable groups (esters, amides, carbonates, carbamates, hydrazones, etc), enzymatically cleavable peptide sequences, self-cyclizing groups, and reducible disulfides.

Additional Modifications of the Conjugate

The compounds of the invention further comprise a functional moiety covalently linked to the scaffold moiety. The functional moiety can comprise a cell-targeting peptidic moiety, a cell-penetrating peptidic moiety, a fusogenic peptidic moiety, a histidine-rich moiety, a fluorophore, or a residue of a second drug molecule.

A fluorophore is a compound or chemical fragment that can emit a fluorescent signal when excited by an appropriate wavelength of light. In certain embodiments, a fluorophore emits light in the visible or near-infrared (NIR) spectrum. Exemplary fluorophores that can be incorporated into the compounds of the invention include carbocyanine, indocarbocyanine, oxacarbocyanine, thiocarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS. In certain embodiments, the fluorophore is a boron-dipyrromethene (BODIPY), coumarin, anthracene, tetrapyrrole, or cyanine derivative, any of which is optionally substituted.

A cell-targeting peptidic moiety is a peptidic group that binds to a cell-surface receptor and can promote receptor-mediated endocytosis of the compound covalently attached to the cell-targeting peptidic moiety. In certain embodiments, the cell targeted by the cell-targeting peptidic moiety is a cancer cell. In certain embodiments, the cell targeted by the cell-targeting peptidic moiety is a dysfunctional skeletal muscle cell, a cardiac cell, a pancreatic cell, a brain cell, or a kidney cell. An exemplary cell-targeting peptide moiety comprises Asp-Arg-Val-Tyr-Ile-His-Pro-Phe (SEQ ID NO: 4). In another example embodiment, an infarcted myocardial cell could be targeted by use of an angiotensin II peptidic moiety, which targets the ATI receptor.

A cell-penetrating peptidic moiety is a peptidic group that facilitates non-receptor-mediated translocation of a compound (e.g., a compound of the invention) through the membrane. The uptake of a compound into a cell can occur via direct translocation or endocytosis. In certain embodiments, the amino acid sequence of the cell-penetrating peptidic moiety is about 5 to about 30 amino acid residues long. In certain embodiments, the amino acid sequence of the cell-penetrating peptidic moiety includes at least 20% or at least 30% positively charged amino acid residues. Exemplary cell-penetrating peptidic moieties include, but are not limited to, HIV-derived Tat peptide sequences, penetratin, oligoarginine, poly-lysine, and derivatives thereof.

A fusogenic peptidic moiety is a peptidic moiety that facilitates fusion of cells. In certain embodiments, a fusogenic peptidic moiety or a fusogenic peptide increase the slow rate of fusion by off-setting a kinetically unfavorable fusion of the membrane-phospholipid bilayers with energetically favorable conformational changes of the peptide.

A histidine-rich moiety is a peptidic moiety containing more than one histidine residue. A histidine-rich moiety can enable effective lysosomal or endosomal escape.

In certain embodiments, the residue of a second drug molecule is a residue of a therapeutically active agent such as an antibacterial agent, antifungal agent, antispasmodic agent, anesthetic agent, anti-inflammatory agent such as a nonsteroidal anti-inflammatory (NSAID) agent, anti-cancer therapeutic agent, calcium channel blocker, antibiotic agent, immunosuppressant, antiviral agent, anti-proliferative agent, antimicrobial agent, antioxidant, nerve-growth inducing agent, photodynamic therapy agent, or smooth muscle relaxant.

In certain embodiments, the functional moiety is covalently linked to the scaffold moiety through one or more covalent bonds. Exemplary covalent bonds through which the functional moiety can be attached to the scaffold moiety include amide, carbonate, carbamate, ether, ester, sulfonate, and sulfamate. The functional moiety can be covalently attached to the scaffold any substitutable position of the functional moiety.

In certain embodiments, the compound of the invention is (SEQ ID NO: 5)

H—Met-Leu-Arg-Ala-Ala-Leu-Ser-Thr-Ala-Arg-Arg-Gly-Pro-Arg-Leu-Ser-Arg-Leu-Leu-Cys-Lys—CONH₂ or a pharmaceutically acceptable salt thereof.

Compositions of the Conjugate

In certain embodiments, the invention also provides pharmaceutical compositions, comprising a compound of the invention and a pharmaceutically acceptable excipient.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs.

In certain embodiments, the composition is a form suitable for injection, systemic administration, or topical administration. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch.

The composition can also be present in a solution or suspension suitable for topical administration. The topically applicable form of the composition can a transdermal patch, ointment, cream, gel, suspension, liquid, elixir, or eye drop.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods of Treatment

In certain embodiments, the invention relates to methods of treating diseases relating to angiotensin-related mitochondrial dysfunction. Therapeutic applications of Mitochondrial Angiotensin Receptor Blockers (MARB) include: (1) Prevent oxidative damage associated with ischemia, MI, diabetes, neurodegenerative diseases and connective tissue disease (e.g., Marfan syndrome) (2) Initiating mitochondrial signal for apoptosis in cases of cancer (3) Inhibit the mitochondrial permeability transition in heart attack and stroke; (4) uncouple the electron transport chain in obesity and diabetes (5) Acceleration of wound healing and fracture repair.

In certain embodiments, the invention provides methods of treating a disorder associated with mitochondrial dysfunction, comprising administering to a subject in need thereof an effective amount of a compound described herein.

In certain embodiments, the disorder is ischemia, myocardial infarction, diabetes, neurodegenerative disease, connective tissue disease, sarcopenia, frailty, heart failure, generalized weakness, or a seizure disorder. In certain embodiments, the subject is a mammal, for example a human.

In certain embodiments, the invention provides methods of treating an angiotensin-mediated disorder, comprising administering to a subject in need thereof an effective amount of a compound described herein.

In certain embodiments, the invention provides methods of treating cancer, comprising administering to a subject in need thereof an effective amount of a compound described herein.

EXAMPLES

Example 1: Synthesis of MTS-Losartan-5-FAM Conjugate

To illustrate the concept of MTS-mediated selective delivery of a MARB to the mitochondria, the $AT_1R$ antagonist Losartan (Ls) was conjugated to a rat liver aldehyde dehydrogenase presequence, MLRAALSTARRGPRLSRLL (abbreviated herein as $MTS_1$) (SEQ ID NO: 1), which can target the inner membrane of the mitochondrion. The fluorescent dye 5-carboxyfluorescein (5-FAM), was attached to allow visualization of the localization of the conjugate.

The formula of the conjugate can be represented by the following formula:

wherein:
M is the peptidic mitochondrial targeting signal from the rat liver aldehyde dehydrogenase precursor (MLRAALSTARRGPRLSRLL) (SEQ ID NO: 1);
X is the dipeptide Cys-Lys;
$L_1$ is an α-thioether ester moiety;
D is the $AT_1R$ antagonist Losartan;
$L_2$ is an amide bond; and
P is the fluorescent dye 5-carboxyfluorescein (5-FAM).

Figure 1:
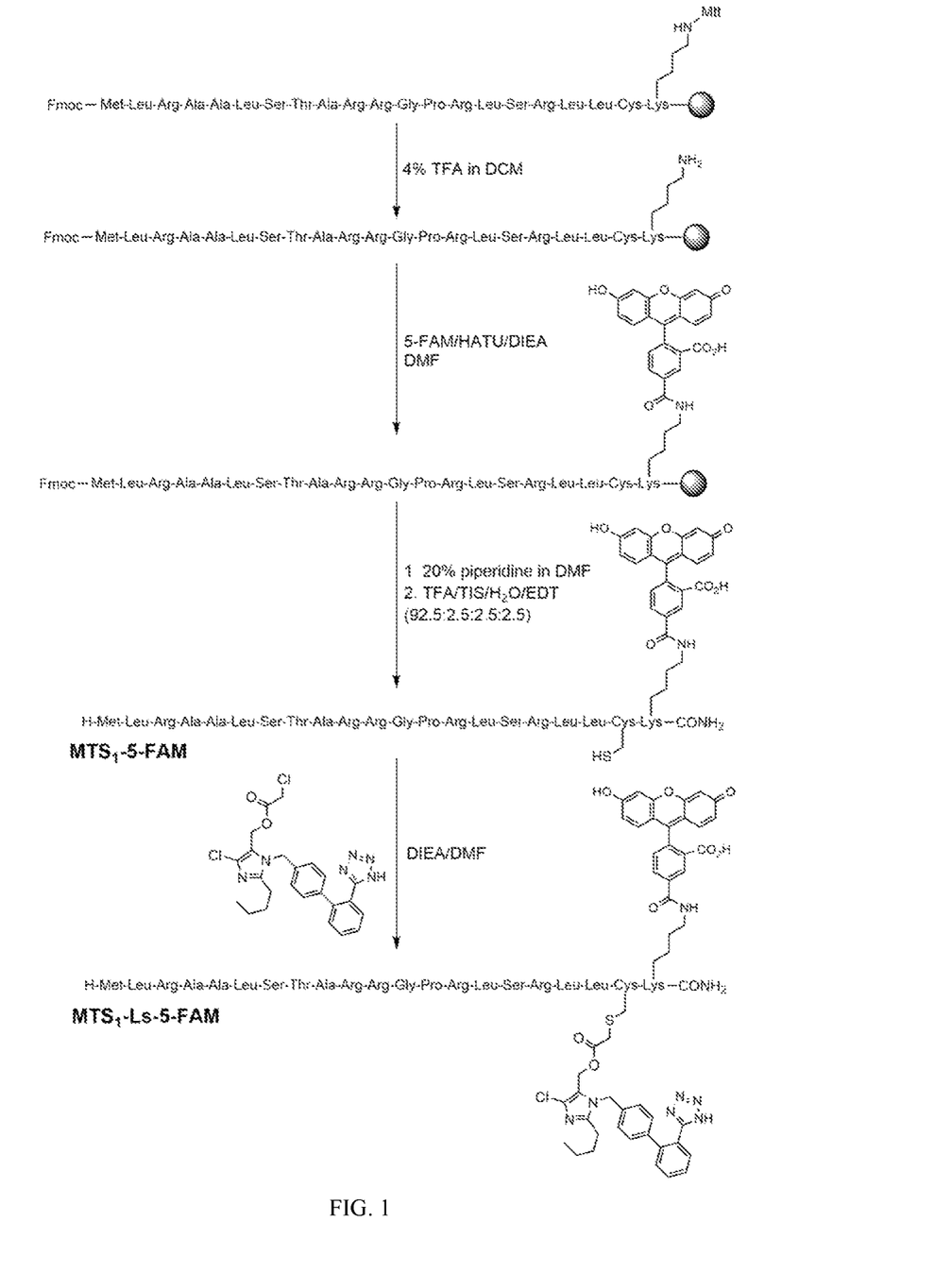
FIG. 1 shows a synthetic scheme for the synthesis of MTS1-Ls-5-FAM. (All of the compounds include SEQ ID NO: 5).

The synthesis of this conjugate is illustrated in FIG. 1. Briefly, the protected peptide MLRAALSTARRG-PRLSRLLCK(Mtt) (SEQ ID NO: 5) was synthesized on a Rink resin using an automated peptide synthesizer and standard Fmoc solid-phase synthesis protocols. Mtt is the acid-sensitive protecting group 4-methyltrityl. Selective removal of the Mtt group gave a free lysine side-chain amine that was coupled with 5-FAM using HBTU/DIPEA. Following cleavage from the resin and subsequent reversed phase HPLC purification, the 5-FAM-conjugated peptide was reacted with the chloroacetic acid ester of Losartan in dimethylformamide. Nucleophilic substitution of the chloride group by the cysteine thiol gave the desired conjugate, $MTS_1$-Ls-5-FAM, which was purified by reversed phase HPLC.

This conjugate was desiged such that cleavage of the MTS peptide by matrix processing peptidases (MPPs) at the C-terminal side of the -LeuLeu- can liberate an free amine on the cysteine, which can cyclize with the chosen linker to release the Losartan (FIG. 2).

Figure 3:
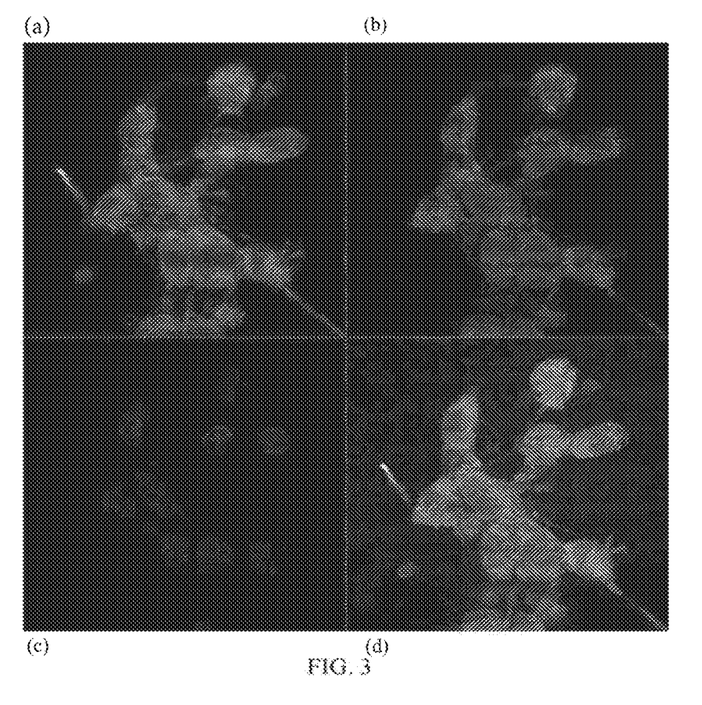
FIG. 3 contains confocal fluorescence microscopy images of rat liver cells incubated with $MTS_1$-Ls-5-FAM for 24 hrs. Panel (a) shows the 5-FAM fluorescence, panel (b) shows the mitochondrial stain (Mitotracker), panel (c) shows the nuclear stain (Hoescht 33342) and panel (d) shows the merged image, indicating the localization of $MTS_1$-Ls-5-FAM within the mitochondria.
Figure 4:
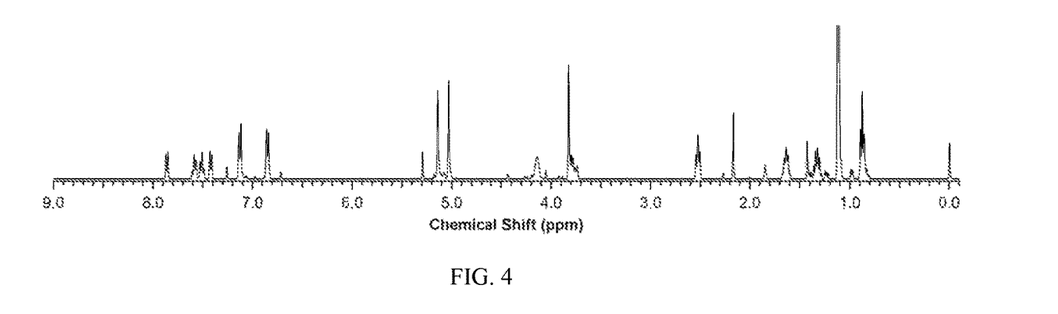
FIG. 4 is a spectrum of the $^1H$ NMR analysis ($CDCl_3$, 400 MHz) of chloroacetyl Losartan.
Figure 5:
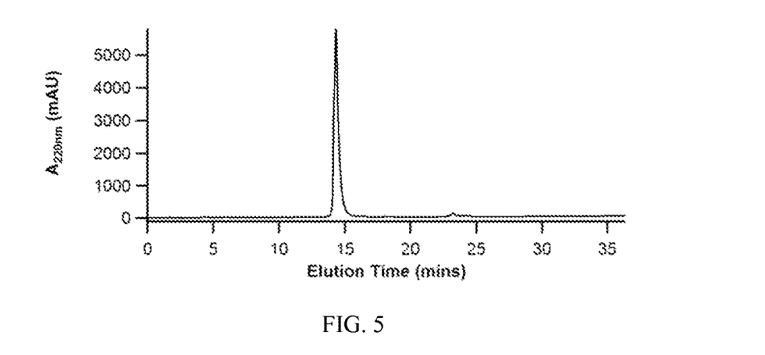
FIG. 5 is an HPLC trace of $MTS_1$-5-FAM.
Figure 6:
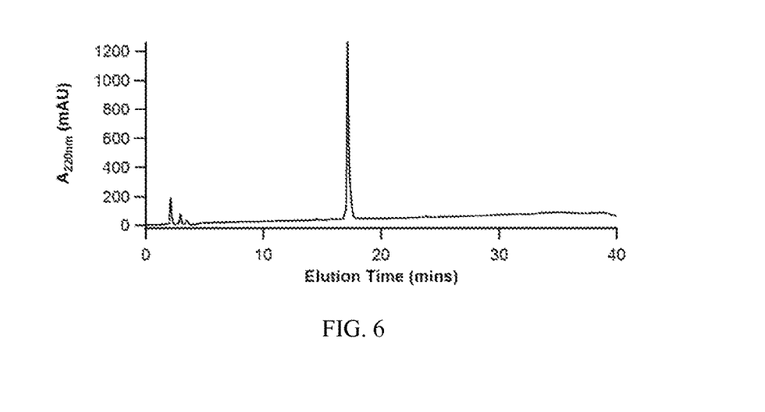
FIG. 6 is an HPLC trace of $MTS_1$-Ls-5-FAM.
Figure 7:
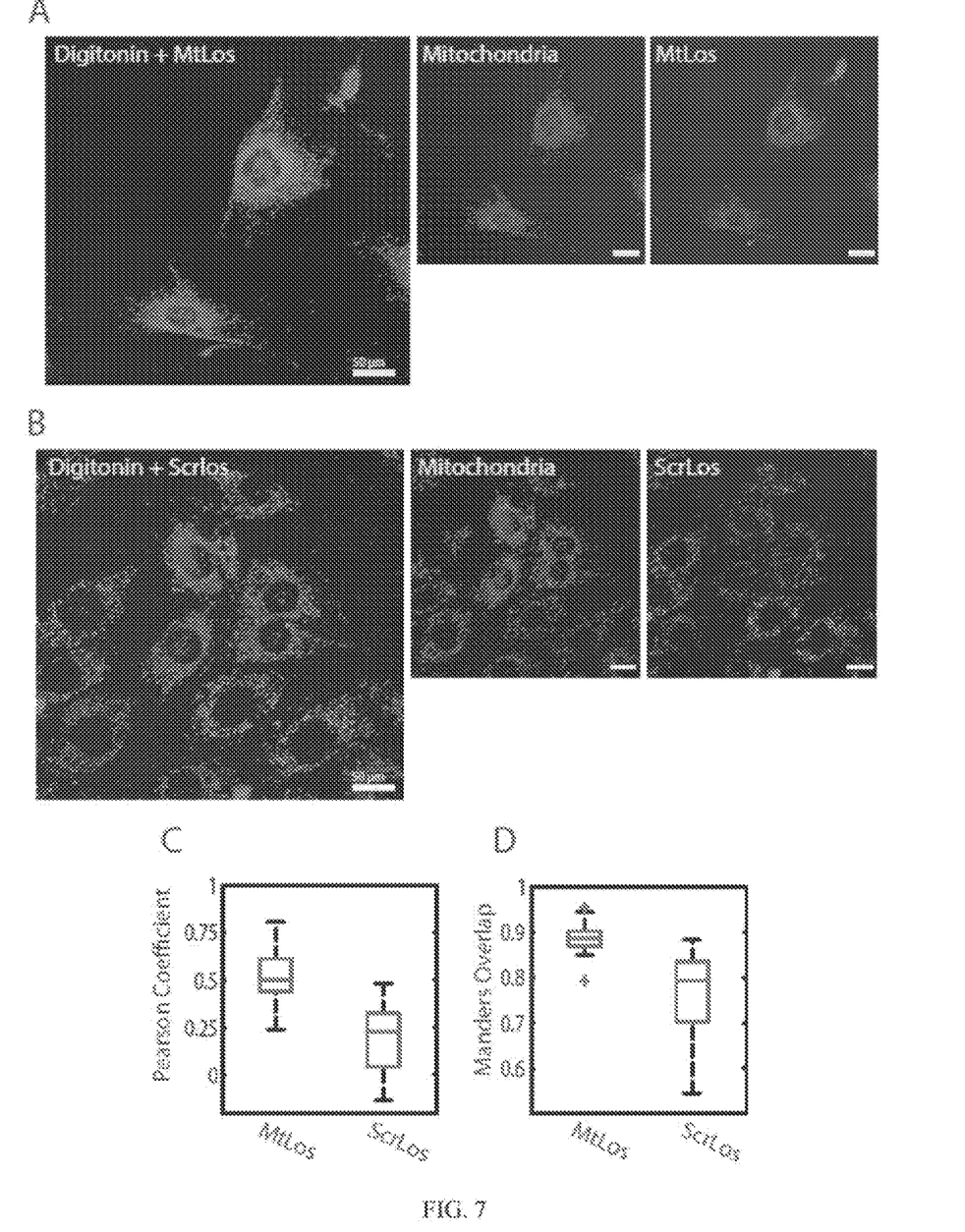
FIG. 7 consists of panels A-D. Panel A shows positive co-localization of $MTS_1$-Ls-5-FAM with mitochondria, panel B shows no co-localization of the scrambled $MTS_1$-Ls-5-FAM with mitochondria of cardiac cells. Panels C and D are show calculations of co-localization using Pearson coefficient (Panel C) and Mander's coefficient (Panel D), which demonstrates that $MTS_1$-Ls-5-FAM is significantly more co-localized with mitochondria based on both Pearson's and Mander's coefficients relative to the scrambled $MTS_1$-Ls-5-FAM.
Figure 8:
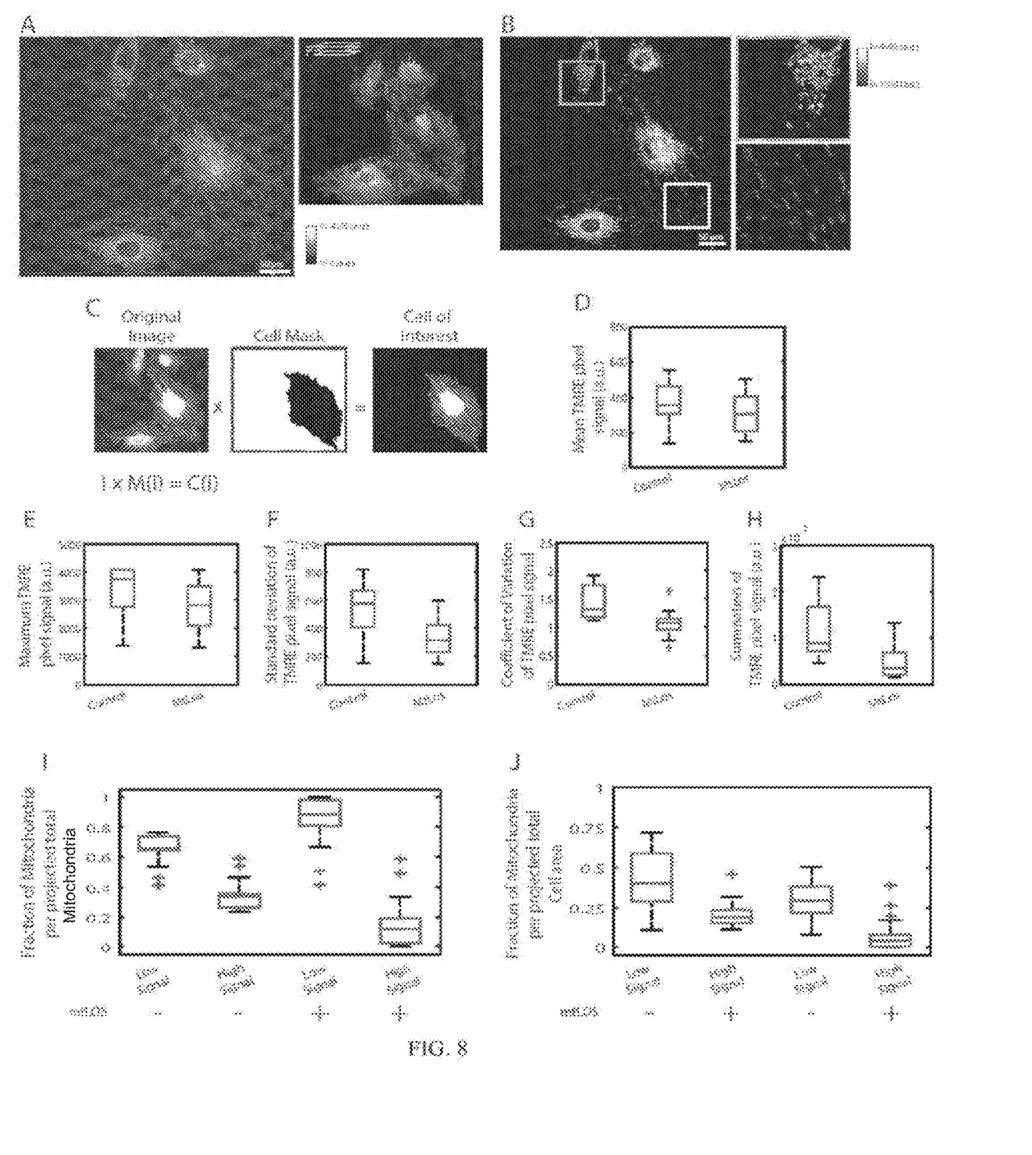

The $MTS_1$-Ls-5-FAM conjugate was transfected into rat cells and incubated for 24 hours before confocal fluorescence microscopy was performed to ascertain cellular localization. Cells were co-stained with Mitotracker-Red and Hoescht 33342 for the mitochondria and nuclei, respectively. Imaging of the cells showed greater than 80% localization of the conjugate with the mitochondria (FIG. 3), confirming that the conjugation of the MTS peptide can selectively target the mitochondria within cells.

Synthetic Protocol

Synthesis of Chloroacetyl Losartan Ester.
Losartan (50 mg, 118 μmol), chloroacetic acid (13.4 mg, 142 μmol) and dimethylaminopyridine (2.8 mg, 27 μmol) were dissolved in THF (4 ml) and cooled to 0° C. Diisopropylcarbodiimide (23 μl, 142 μmol) was added and stirring continued at 0° C. for 90 mins, after which the mixture was allowed to warm to room temperature. The reaction was monitored by thin layer chromatography (5% of (10% $NH_4OH$ in MeOH) in DCM). After overnight stirring, the reaction was deemed complete and the mixture was diluted with DCM (10 ml) and washed with 0.1 M HCl (15 ml) and brine (15 ml). The organic portion was dried over $Na_2SO_4$ and solvents removed in vacuo. Further drying under vacuum gave chloroacetyl Losartan as a white solid that was shown by NMR to be >90% pure (69 mg, quantitative yield).

Synthesis of $MTS_1$-5-FAM.
The protected peptide Fmoc-MLRAALSTARRG-PRLSRLLCK-(Mtt) (SEQ ID NO: 5) was synthesized on a Rink resin (250 μmol) using a Focus XC automated peptide synthesizer (AAPPTEC, Louisville, Ky., USA) and standard Fmoc solid-phase synthesis protocols (Fmoc deprotection: 20% methylpiperidine in DMF; Coupling:amino acid:HBTU:DIEA 4:3.98:6 relative to the amino resin). The Mtt protecting group was removed using TFA/(TIS/DCM (4:5:91), shaking for 5 minutes intervals until no yellow color developed on addition of the reagent and room temperature Kaiser test gave a strong blue color (positive for free amine). The resin was then shaken with a solution of DIEA in DMF to neutralize residual TFA. 5-FAM (142 mg, 377 μmol) and HATU (140 mg, 368 μmol) were dissolved in DMF (5 ml) and DIEA (95 μl, 563 μmol) and allowed to activate for 2 min. The solution was then added to the resin and shaken for 6 hrs. After washing (3×DMF, 3×DCM), a positive Kaiser test was obtained and so the coupling step was repeated. The N-terminal Fmoc group was removed with 20% methylpiperidine in DMF (2×10 ml) and the peptide cleaved from the resin using TFA/TIS/$H_2O$/EDT (92.5:2.5:2.5:2.5) for 3 hrs. The crude peptide was isolated by concentration in vacuo followed by precipitation in cold $Et_2O$. The collected solid was purified by reversed phase HPLC and product identity confirmed by MALDI-T of MS-2728.55 [M+H]$^+$, 1364.87 [M+2H]$^{2+}$.

Synthesis of MTS$_1$-Ls-5-FAM.

MTS$_1$-5-FAM (10.6 mg, 3.9 µmol) was first dissolved in a solution of chloroacetyl Losartan (2.9 mg, 5.8 µmol) in DMF (500 µl) and then DIEA (1.65 µl, 9.8 µmol) was added. The mixture was allowed to react at 4° C. for 3 days, after which HPLC analysis showed 60% conversion to the desired product. The addition of extra DIEA (0.5 µl, 3.0 µmol) showed no further changes and the reaction was deemed to be complete. The mixture as diluted to 8 ml with 0.1% aqueous TFA and purified by reversed phase HPLC. Product-containing fractions were combined and lyophilized to give MTS$_1$-Ls-5-FAM as a yellow powder.

Abbreviations utilized in experimental section: DCM: dichloromethane; DIEA: diisopropylethylamine; DMF: N,N'-dimethylformamide; EDT: ethane-1,2-dithiol; ESI-MS: electrospray ionization mass spectrometry; HATU: O-(7-Azabenzotriazol-1-yl)-1,1,3,3-tetramethyl-uronium hexafluorophosphate; HBTU: O-benzotriazole-N,N,N',N'-tetramethyl-uronium hexafluorophosphate; HPLC: high performance liquid chromatography; MALDI-T of MS: matrix-assisted laser desorption ionization time-of-flight mass spectrometry; Mtt: 4-methyltrityl; TFA: trifluoroacetic acid; THF: tetrahydrofuran; TIS: triisopropylsilane.

REFERENCES

1. Leri A, Claudio P P, Li Q, et al. Stretch-mediated release of angiotensin II induces myocyte apoptosis by activating p53 that enhances the local renin-angiotensin system and decreases the bcl-2-to-bax protein ratio in the cell. *J Clin Invest.* 1998; 101(7): 1326-1342.
2. Leri A, Liu Y, Li B, et al. Up-regulation of AT(1) and AT(2) receptors in postinfarcted hypertrophied myocytes and stretch-mediated apoptotic cell death. *Am J Pathol.* 2000; 156(5): 1663-1672.
3. Sadoshima J, Xu Y, Slayter H S, Izumo S. Autocrine release of angiotensin II mediates stretch-induced hypertrophy of cardiac myocytes in vitro. *Cell.* 1993; 75(5): 977-984.
4. Cook J L, Zhang Z, Re R N. In vitro evidence for an intracellular site of angiotensin action. *Circ Res.* 2001; 89(12): 1138-1146.
5. Robertson A L, Jr, Khairallah P A. Angiotensin II: Rapid localization in nuclei of smooth and cardiac muscle. *Science.* 1971; 172(988): 1138-1139.
6. Wiemer G, Scholkens B A, Wagner A, Heitsch H, Linz W. The possible role of angiotensin II subtype AT2 receptors in endothelial cells and isolated ischemic rat hearts. *J Hypertens Suppl.* 1993; 11(5): S234-5.
7. Ratliff B, Sekulic M, Rodebaugh J, Solhaug M J. Angiotensin II regulates nitric oxide synthase expression in afferent arterioles of the developing porcine kidney. *Pediatr Res.* 2010.
8. Siragy H M, Inagami T, Ichiki T, Carey R M. Sustained hypersensitivity to angiotensin II and its mechanism in mice lacking the subtype-2 (AT2) angiotensin receptor. *Proc Natl Acad Sci USA.* 1999; 96(11): 6506-6510.
9. Siragy H M, de Gasparo M, Carey R M. Angiotensin type 2 receptor mediates valsartan-induced hypotension in conscious rats. *Hypertension.* 2000; 35(5): 1074-1077.
10. Abadir P M, Carey R M, Siragy H M. Angiotensin AT2 receptors directly stimulate renal nitric oxide in bradykinin B2-receptor-null mice. *Hypertension.* 2003; 42(4): 600-604.
11. Gwathmey T M, Shaltout H A, Pendergrass K D, et al. Nuclear angiotensin II type 2 (AT2) receptors are functionally linked to nitric oxide production. *Am J Physiol Renal Physiol.* 2009; 296(6): F1484-93.
12. Michel T, Feron O. Nitric oxide synthases: Which, where, how, and why? *J Clin Invest.* 1997; 100(9): 2146-2152.
13. Bates T E, Loesch A, Burnstock G, Clark J B. Immunocytochemical evidence for a mitochondrially located nitric oxide synthase in brain and liver. *Biochem Biophys Res Commun.* 1995; 213(3): 896-900.
14. Valdez L B, Boveris A. Mitochondrial nitric oxide synthase, a voltage-dependent enzyme, is responsible for nitric oxide diffusion to cytosol. *Front Biosci.* 2007; 12: 1210-1219.
15. Burwell L S, Brookes P S. Mitochondria as a target for the cardioprotective effects of nitric oxide in ischemia-reperfusion injury. *Antioxid Redox Signal.* 2008; 10(3): 579-599.
16. Ghafourifar P, Richter C. Nitric oxide synthase activity in mitochondria. *FEBS Lett.* 1997; 418(3): 291-296.
17. Carreras M C, Peralta J G, Converso D P, et al. Modulation of liver mitochondrial NOS is implicated in thyroid-dependent regulation of O(2) uptake. *Am J Physiol Heart Circ Physiol.* 2001; 281(6): H2282-8.
18. Lee J H, Xia S, Ragolia L. Upregulation of AT2 receptor and iNOS impairs angiotensin II-induced contraction without endothelium influence in young normotensive diabetic rats. *Am J Physiol Regul Integr Comp Physiol.* 2008; 295(1): R144-54.
19. Dedkova E N, Blatter L A. Characteristics and function of cardiac mitochondrial nitric oxide synthase. *J Physiol.* 2009; 587(Pt 4): 851-872.
20. Lacza Z, Pankotai E, Csordas A, et al. Mitochondrial N O and reactive nitrogen species production: Does mtNOS exist? *Nitric Oxide.* 2006; 14(2): 162-168.
21. Ghafourifar P, Richter C. Nitric oxide synthase activity in mitochondria. *FEBS Lett.* 1997; 418(3): 291-296.
22. Pfanner N, Geissler A. Versatility of the mitochondrial protein import machinery. *Nat. Rev. Mol. Biol.* 2001; 2: 339-349.
23. Flierl A, Jackson C, Cottrell B, Murdock D, Seibel P, Wallace D C. Targeted delivery of DNA to the mitochondrial compartment via import sequence-conjugated peptide nucleic acid. Molecular Therapy. 2003; 7(4): 550-557.
24. Bruch M D, Hoyt D W. Conformational Analysis of a mitochondrial presequence derived from the F1-ATPase Beta-subunit by C D and NMR spectroscopy. Biochimica Et Biophysica Acta. 1992; 1159(1): 81-93.
25. Hammen P K, Gorenstein D G, Weiner H. Structure of the signal sequences for 2 mitochondrial matrix proteins that are not proteolytically processed upon import. Biochemistry. 1994; 33(28): 8610-7.
26. Karslake C, Piotto M E, Pak Y K, Weiner H, Gorenstein D G. 2D-NMR and structural model for a mitochondrial signal peptide bound to a micelle. Biochemistry. 1990; 29(42): 9872-8.
27. Regev-Rudzki, N. et al., "The mitochondrial targeting sequence tilts the balance between mitochondrial and cytosolic dual localization" J. Cell. Sc. 2008, 121, 2423.
28. Battigelli, A., et al. Peptide-based carbon nanotubes for mitochondrial targeting. Nanoscale, 2013, 5, 9110.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound, comprising:
a mitochondrial targeting signal, wherein the mitochondrial targeting signal is a peptidic moiety;
a residue of a drug molecule;
a functional moiety; and
a scaffold moiety;
wherein the mitochondrial targeting signal, the residue of a drug molecule, and the functional moiety are each covalently linked to the scaffold moiety;
wherein the functional moiety comprises a cell-targeting peptidic moiety, a cell-penetrating peptidic moiety, a fusogenic peptidic moiety, a histidine-rich moiety, a fluorophore, or a residue of a second drug molecule;
wherein the fluorophore is selected from the group consisting of optionally substituted boron-dipyrromethene (BODIPY), coumarin, anthracene, tetrapyrrole, fluorescein and cyanine derivatives; and
wherein the scaffold moiety comprises one or more covalent bonds, wherein at least one bond is selected from amide, carbonate, carbamate, ether, ester, sulfonate, and sulfamate.

2. The compound of claim 1, wherein the mitochondrial targeting signal selectively directs delivery of the compound to a compartment of the mitochondrion.

3. The compound of claim 2, wherein the compartment of the mitochondrion is selected from the group consisting of an outer membrane, an inner membrane, and inter-membrane space, and a mitochondrial matrix.

4. The compound of claim 1, wherein the mitochondrial targeting signal is recognized and cleaved by a mitochondrial peptidase.

5. The compound of claim 1, wherein the mitochondrial targeting signal comprises about 10 to about 70 amino acid residues.

6. The compound of claim 1, wherein the mitochondrial targeting signal comprises an amino acid sequence having at least 50% sequence homology to Met-Leu-Arg-Ala-Ala-Leu-Ser-Thr-Ala-Arg-Arg-Gly-Pro-Arg-Leu-Ser-Arg-Leu-Leu (SEQ ID NO: 1), Met-Leu-Ser-Ala-Arg-Ser-Ala-Ile-Lys-Arg-Pro-Ile-Val-Arg-Gly-Leu-Ala-Thr-Val (SEQ ID NO: 2), or Met-Ser-Val-Leu-Thr-Pro-Leu-Leu-Leu-Arg-Gly-Leu-Thr-Gly-Ser-Ala-Arg-Arg-Leu-Pro-Val-Pro-Arg-Ala-Lys (SEQ ID NO: 3).

7. The compound of claim 6, wherein the amino acid sequence has at least 50% sequence homology to Met-Leu-Arg-Ala-Ala-Leu-Ser-Thr-Ala-Arg-Arg-Gly-Pro-Arg-Leu-Ser-Arg-Leu-Leu (SEQ ID NO: 1).

8. The compound of claim 1, wherein the mitochondrial targeting signal is covalently linked to the scaffold moiety through one or more covalent bonds, wherein at least one bond is selected from amide, carbonate, carbamate, ether, ester, sulfonate, and sulfamate.

9. The compound of claim 1, wherein the scaffold moiety comprises a peptide fragment, an oligocarboxylate, or an oligomeric moiety.

10. The compound of claim 9, wherein the scaffold moiety comprises one or more functionalizable heteroatoms.

11. The compound of claim 9, wherein the scaffold moiety comprises a peptide fragment, the peptide fragment comprising at least one amino acid residue selected from Arg, Lys, Asp, Glu, Ser, Thr, Asn, Gin, Cys, Sec, and Pro.

12. The compound of claim 11, wherein the scaffold moiety comprises a peptide fragment comprising at least one amino acid residue selected from Lys, Asp, Glu, and Cys.

13. The compound of claim 12, wherein the scaffold moiety comprises Cys-Lys.

14. The compound of claim 1, wherein the scaffold moiety comprises a peptide fragment and wherein the mitochondrial targeting signal forms a continuous peptide chain with the scaffold moiety.

15. The compound of claim 14, wherein an N-terminus of the peptide fragment of the scaffold moiety is attached to the mitochondrial targeting signal.

16. The compound of claim 1, wherein the drug molecule binds to an angiotensin receptor.

17. The compound of claim 1, wherein the drug molecule binds to an $AT_1$-type receptor and/or an $AT_2$-type receptor.

18. The compound of claim 1, wherein the drug molecule is an angiotensin receptor blocker.

19. The compound of claim 1, wherein the drug molecule is selected from the group consisting of valsartan, telmisartan, losartan, irbesartan, azilsartan, olmesartan, candesartan, and ephrosartan.

20. The compound of claim 1, wherein the residue of the drug molecule is covalently linked to the scaffold moiety through one or more covalent bonds, wherein at least one bond is selected from amide, carbonate, carbamate, ether, ester, sulfonate, and sulfamate.

21. The compound of claim 20, wherein one or more covalent bonds linking the residue of the drug molecule to the scaffold moiety are cleaved in the mitochondria.

22. The compound of claim 1, wherein cell-targeting peptidic moiety binds to a receptor expressed on the surface of a cell.

23. The compound of claim 1, wherein the cell-penetrating peptidic moiety comprises about 5 to about 30 amino acid residues, wherein at least 30% of the amino acid residues are positively charged.

24. The compound of claim 23, wherein the cell-penetrating peptidic moiety comprises an HIV trans-activating transcriptional activator, penetratin, a polyarginine, or a polylysine.

25. The compound of claim 1, wherein the functional moiety is covalently linked to the scaffold moiety through one or more covalent bonds, wherein at least one bond is selected from amide, carbonate, carbamate, ether, ester, sulfonate, and sulfamate.

26. The compound of claim 13, wherein the C-terminus of the scaffold moiety is amidated.

27. The compound of claim 1, having the following structure:

(SEQ ID NO: 5)

or a pharmaceutically acceptable salt thereof.

28. A pharmaceutical composition comprising the compound of claim 1 and a pharmaceutically acceptable excipient.

29. The composition of claim 28, in a form suitable for injection.

30. The composition of claim 28, in a form suitable for systemic administration.

31. The composition of claim 30, wherein the composition is selected from capsules, tablets, and gelcaps.

32. The composition of claim 28, in a form suitable for topical application.

33. The composition of claim 32, wherein the topically applicable form is selected from a transdermal patch, ointment, cream, gel, suspension, liquid, elixir, and eye drop.

34. A method of treating a disorder associated with mitochondrial dysfunction, comprising administering to a subject in need thereof an effective amount of a compound of claim 1.

35. The method of claim 34, wherein the disorder is ischemia, myocardial infarction, diabetes, neurodegenerative disease, connective tissue disease, sarcopenia, frailty, heart failure, generalized weakness, or a seizure disorder.

36. The method of claim 34, wherein the subject is a mammal.

37. The method of claim 34, wherein the subject is a human.

38. A method of treating an angiotensin-mediated disorder, comprising administering to a subject in need thereof an effective amount of a compound of claim 1.

39. A method of treating cancer, comprising administering to a subject in need thereof an effective amount of a compound of claim 1.

40. The compound of claim 1, wherein the fluorescein is 5-carboxyfluorescein (5-FAM).

* * * * *